United States Patent
Guo

(10) Patent No.: US 8,143,265 B2
(45) Date of Patent: Mar. 27, 2012

(54) METHOD OF TREATING ATHEROSCLEROSIS

(75) Inventor: ZhongMao Guo, Franklin, TN (US)

(73) Assignee: Meharry Medical College, Nashville, TN (US)

( * ) Notice: Subject to any disclaimer, the term of this patent is extended or adjusted under 35 U.S.C. 154(b) by 601 days.

(21) Appl. No.: 12/101,444

(22) Filed: Apr. 11, 2008

(65) Prior Publication Data

US 2008/0255050 A1  Oct. 16, 2008

Related U.S. Application Data

(60) Provisional application No. 60/911,931, filed on Apr. 16, 2007.

(51) Int. Cl.
*A61K 31/52* (2006.01)
*A61K 38/00* (2006.01)

(52) U.S. Cl. .................... 514/263.4; 514/1.9; 514/263.1; 544/277

(58) Field of Classification Search ............ 514/1.9, 514/263.4, 263.1; 544/277
See application file for complete search history.

(56) References Cited

U.S. PATENT DOCUMENTS

| | | | |
|---|---|---|---|
| 6,255,485 B1 * | 7/2001 | Gray et al. | ............ 544/277 |
| 6,900,307 B1 | 5/2005 | Sasaki et al. | |
| 7,138,401 B2 | 11/2006 | Kasibhatla et al. | |

FOREIGN PATENT DOCUMENTS

EP  0355986 B1  2/1990

OTHER PUBLICATIONS

Hosoi et al, European Journal of Pharmacology, 553, 2006, 61-66.*
Beltowski, Atherosclerosis 189, 2006), 47-60.*
Davignon et al, Clinica Chemica Acta 286, 1999, pp. 115-143.*
Merriam-Webster online Dictionary, prevent definition, accessed online Feb. 17, 2009.*
Wu D et al. 2-aminopurine inhibits lipid accumulation induced by apolipoprotein E-deficient lipoprotein in macrophages: potential role of eukaryotic initiation factor-2α phosphorylation in foam cell formation. Journal of Pharmacology and Experimental Therapeutics. 2008; 326(2): 395-405.

* cited by examiner

*Primary Examiner* — James D Anderson
*Assistant Examiner* — Savitha Rao
(74) *Attorney, Agent, or Firm* — Myers Bigel Sibley & Sajovec, P.A.

(57) ABSTRACT

A method of treating atherosclerosis in a subject is carried out by administering the subject 2-aminopurine or a pharmaceutically salt thereof in a treatment effective amount. Optionally, the subject may also be administered an additional hypolipidemic agent. Compositions useful for carrying out the present invention are also described.

8 Claims, 2 Drawing Sheets

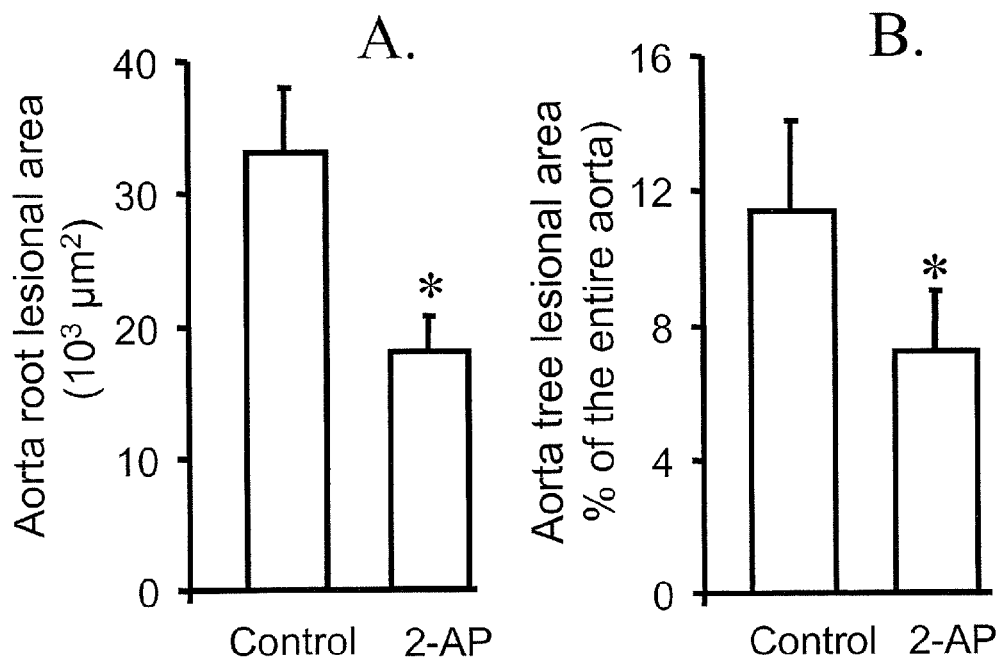
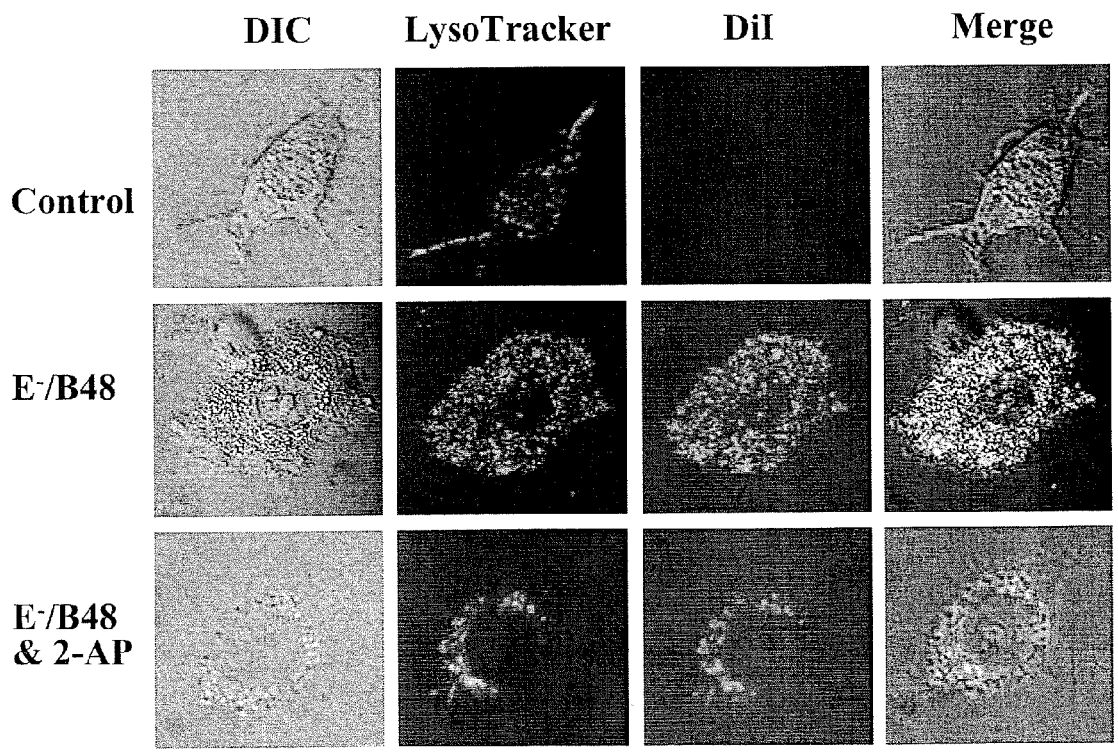
Figure 1
Figure 2

METHOD OF TREATING ATHEROSCLEROSIS

RELATED APPLICATIONS

This application claims the benefit of U.S. provisional patent application Ser. No. 60/911,931, filed Apr. 16, 2007, the disclosure of which is incorporated by reference herein in its entirety.

FIELD OF THE INVENTION

The present invention concerns methods of treating atherosclerosis.

BACKGROUND OF THE INVENTION

Atherosclerosis is the underlying mechanism of ischemic heart disease and stroke, which represent the most common cause of death in the United States. Atherogenesis starts from the deposition of ApoB-containing lipoproteins, such as low-density lipoproteins and chylomicron remnants, in the intima of the arterial wall. Macrophages then take up the deposited lipoproteins and transform into foam cells[1]. The presence of foam cells in the arterial intima is a hallmark feature of atherosclerosis. Continued accumulation of lipid and lipid-laden foam cells, and the succeeded proliferation of smooth muscle and connective tissue give rise to atherosclerotic plaques. Rupture of a plaque triggers thrombosis and/or embolism that may cause luminal occlusion in coronary or cerebral arteries, resulting in heart attack and stroke[1,2].

SUMMARY OF THE INVENTION

A first aspect of the present invention is a method of treating atherosclerosis or hyperlipidemia in a subject in need thereof, comprising administering said subject 2-aminopurine or a pharmaceutically salt thereof in an amount effective to treat said atherosclerosis or hyperlipidemia.

A second aspect of the invention is a composition comprising 2-aminopurine in a pharmaceutically acceptable carrier, alone or in combination with at least one additional hypolipidemic agent.

A further aspect of the present invention is the use of an active agent as described above for the preparation of a medicament for the treatment of a disease or condition as described herein.

BRIEF DESCRIPTION OF THE DRAWINGS

FIG. 1. ApoE$^{-/-}$ mice at 5 weeks of age were treated with 200 mg/kg BW of 2-AP or equal volume of water as control via gavage feeding. This procedure was repeated once every other day for 24 consecutive weeks. A. Heart-aorta samples were collected from mice at 6 months of age (n=12 for each group of mice). Sequential 8-μm thick sections were cut from the mouse aortic root. The area (μm$^2$) of atherosclerotic lesions in the section was measured. B. Aortas from the aortic root to the iliac bifurcation were collected, and the area of atherosclerotic lesions and the total area of the aortic surface were measured, data are expressed as the percent of aortic surface area covered by atherosclerotic lesions. Data are expressed as the mean±SEM. *P<0.05 as compared to untreated control mice.

FIG. 2. Mouse peritoneal macrophages were treated with 20 μg/ml DiI-labeled E$^-$/B48 lipoproteins, 20 μg/ml E$^-$/B48 lipoproteins plus 2 mM 2-AP, or culture medium alone (control) for 48 hrs. The cells were then stained with LysoTracker, which is used to localize lysosomes. Confocal microscopy images were captured, and the merged images are an overlay of the differential interference contrast (DIC) images and the fluorescence images of intracellular DiI and LysoTracker staining. Co-localization of DiI and LysoTracker staining indicates lipoprotein accumulation in the lysosomes.

DETAILED DESCRIPTION OF PREFERRED EMBODIMENTS

Figure 3:
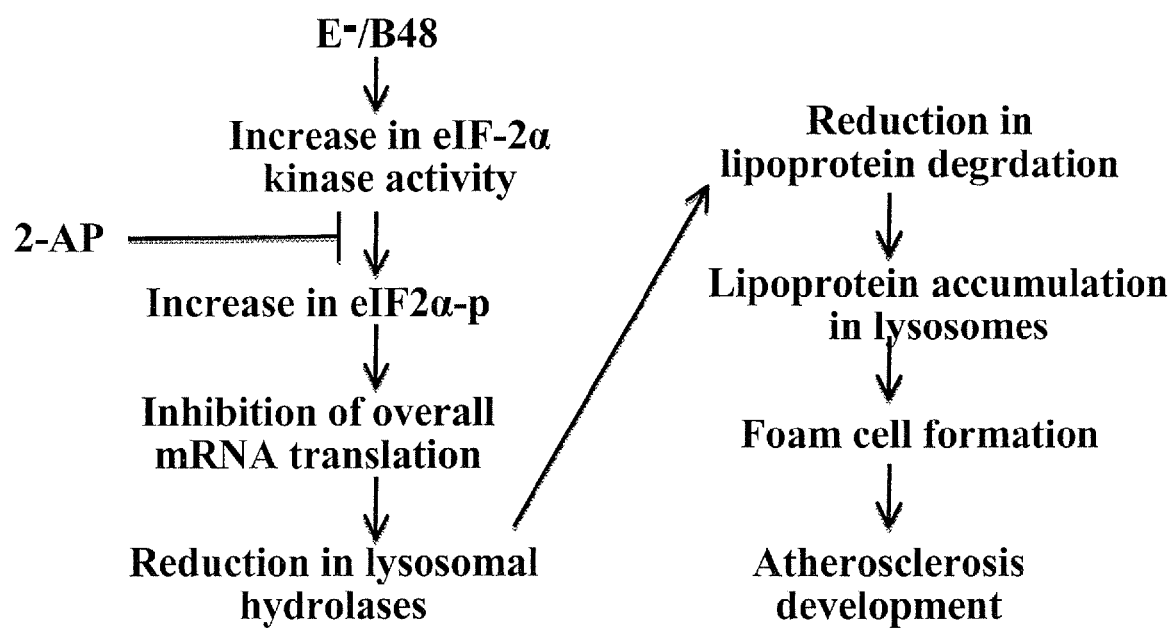
FIG. 3. Schematic diagram of a proposed mechanism of the present invention.

The present invention is primarily concerned with the treatment of human subjects, but the invention may also be carried out on animal subjects, particularly mammalian subjects such as dogs, cats, livestock and horses for veterinary purposes. While subjects may be of any suitable age, the subjects are in some embodiments adult or geriatric subjects.

"Treat" as used herein refers to any type of treatment that imparts a benefit to a patient, particularly delaying or retarding the progression of atherosclerosis.

"Pharmaceutically acceptable" as used herein means that the compound or composition is suitable for administration to a subject to achieve the treatments described herein, without unduly deleterious side effects in light of the severity of the disease and necessity of the treatment.

"Additional hypolipidemic agent" (or "antiatherogenic agent") as used herein include but are not limited to HMG-CoA reductase inhibitors or "statins" (including but not limited to Atorvastatin, Cerivastatin, Fluvastatin, Lovastatin, Mevastatin, Pitavastatin, Pravastatin, Rosuvastatin, Simvastatin, etc.), Bile acid sequestrants or bile acid resins (including but not limited to Cholestyramine, Colesevelam, Colestipol, etc.); fibrates or fibric acid derivatives (including but not limited to Fenofibrate and Gemfibrozil), niacin, ezetimibe, phytosterols, CETP Inhibitors (cholesteryl ester transfer protein inhibitors), squalene synthase inhibitors, ApoA-1 Milano, AGI-1067, etc. These compounds are also sometimes referred to as "active compounds" herein.

"Concurrently" as used herein means sufficiently close in time to produce a combined effect (that is, concurrently may be simultaneously, or it may be two or more events occurring within a short time period before or after each other).

1. Active Compounds.

2-aminopurine (sometimes also referred to as an "active compound" or "active agent" herein), is known and has the structure:

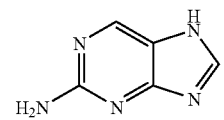

2-aminopurine has the IUPAC name 7H-purin-2-amine and has been assigned CAS number 452-06-2. See also P. M. Kincey, EP0355986.

The active compounds disclosed herein can, as noted above, be prepared in the form of their pharmaceutically acceptable salts. Pharmaceutically acceptable salts are salts that retain the desired biological activity of the parent compound and do not impart undesired toxicological effects. Examples of such salts are (a) acid addition salts formed with inorganic acids, for example hydrochloric acid, hydrobromic acid, sulfuric acid, phosphoric acid, nitric acid and the like;

and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; (b) salts formed from elemental anions such as chlorine, bromine, and iodine, and (c) salts derived from bases, such as ammonium salts, alkali metal salts such as those of sodium and potassium, alkaline earth metal salts such as those of calcium and magnesium, and salts with organic bases such as dicyclohexylamine and N-methyl-D-glucamine.

2. Pharmaceutical Formulations.

The active compounds described above may be formulated for administration in a pharmaceutical carrier in accordance with known techniques. See, e.g., Remington, *The Science And Practice of Pharmacy* (9$^{th}$ Ed. 1995). In the manufacture of a pharmaceutical formulation according to the invention, the active compound (including the physiologically acceptable salts thereof) is typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.01 or 0.5% to 10, 50, or 95% or 99% by weight of each of the active compounds (as described above, and/or including additional hypolipidemic active agents). One or more active compounds may be incorporated in the formulations of the invention, which may be prepared by any of the well known techniques of pharmacy comprising admixing the components, optionally including one or more accessory ingredients.

The formulations of the invention include those suitable for oral, rectal, topical, buccal (e.g., sub-lingual), vaginal, parenteral (e.g., subcutaneous, intramuscular, intradermal, or intravenous), topical (i.e., both skin and mucosal surfaces, including airway surfaces) and transdermal administration, although the most suitable route in any given case will depend on the nature and severity of the condition being treated and on the nature of the particular active compound which is being used.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations suitable for buccal (sub-lingual) administration include lozenges comprising the active compound in a flavoured base, usually sucrose and acacia or tragacanth; and pastilles comprising the compound in an inert base such as gelatin and glycerin or sucrose and acacia.

Formulations of the present invention suitable for parenteral administration comprise sterile aqueous and non-aqueous injection solutions of the active compound(s), which preparations are preferably isotonic with the blood of the intended recipient. These preparations may contain anti-oxidants, buffers, bacteriostats and solutes which render the formulation isotonic with the blood of the intended recipient. Aqueous and non-aqueous sterile suspensions may include suspending agents and thickening agents. The formulations may be presented in unit\dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described. For example, in one aspect of the present invention, there is provided an injectable, stable, sterile composition comprising an active compound(s), or a salt thereof, in a unit dosage form in a sealed container. The compound or salt is provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent which is physiologically acceptable may be employed in sufficient quantity to emulsify the compound or salt in an aqueous carrier. One such useful emulsifying agent is phosphatidyl choline.

Formulations suitable for rectal administration are preferably presented as unit dose suppositories. These may be prepared by admixing the active compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3 (6):318 (1986)) and typically take the form of an optionally buffered aqueous solution of the active compound. Suitable formulations comprise citrate or bis\tris buffer (pH 6) or ethanol/water and contain from 0.1 to 0.2M active ingredient.

Further, the present invention provides liposomal formulations of the compounds disclosed herein and salts thereof. The technology for forming liposomal suspensions is well known in the art. When the compound or salt thereof is an aqueous-soluble salt, using conventional liposome technology, the same may be incorporated into lipid vesicles. In such an instance, due to the water solubility of the compound or salt, the compound or salt will be substantially entrained within the hydrophilic center or core of the liposomes. The lipid layer employed may be of any conventional composition and may either contain cholesterol or may be cholesterol-free. When the compound or salt of interest is water-insoluble, again employing conventional liposome formation technology, the salt may be substantially entrained within the hydrophobic lipid bilayer which forms the structure of the liposome. In either instance, the liposomes which are produced may be reduced in size, as through the use of standard sonication and homogenization techniques.

Of course, the liposomal formulations containing the compounds disclosed herein or salts thereof, may be lyophilized to produce a lyophilizate which may be reconstituted with a pharmaceutically acceptable carrier, such as water, to regenerate a liposomal suspension.

Other pharmaceutical compositions may be prepared from the water-insoluble compounds disclosed herein, or salts thereof, such as aqueous base emulsions. In such an instance, the composition will contain a sufficient amount of pharmaceutically acceptable emulsifying agent to emulsify the desired amount of the compound or salt thereof. Particularly useful emulsifying agents include phosphatidyl cholines, and lecithin.

In addition to active compound(s), the pharmaceutical compositions may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. Of course, as indicated, the pharmaceutical compositions of the present invention may be lyophilized using techniques well known in the art.

The active compounds described herein may be prepared in compositions alone or in combination with at least one additional hypolipidemic drug.

Dosage and Routes of Administration.

As noted above, the present invention provides pharmaceutical formulations comprising the active compounds (including the pharmaceutically acceptable salts thereof), in pharmaceutically acceptable carriers for oral, rectal, topical, buccal, parenteral, intramuscular, intradermal, or intravenous, and transdermal administration.

The therapeutically effective dosage of any specific active compound, the use of which is in the scope of present invention, will vary somewhat from compound to compound, and patient to patient, and will depend upon the condition of the patient and the route of delivery. As a general proposition, a dosage from about 0.1 to about 50 mg/kg will have therapeutic efficacy, with all weights being calculated based upon the weight of the active compound, including the cases where a salt is employed. Toxicity concerns at the higher level may restrict intravenous dosages to a lower level such as up to about 10 mg/kg, with all weights being calculated based upon the weight of the active base, including the cases where a salt is employed. A dosage from about 10 mg/kg to about 50 mg/kg may be employed for oral administration. Typically, a dosage from about 0.5 mg/kg to 5 mg/kg may be employed for intramuscular injection.

The present invention is explained in greater detail in the following non-limiting Examples.

EXAMPLE 1

Potential relevance of ApoE deficiency to human atherosclerosis: Human ApoE is a polymorphic protein with three common isoforms, known as ApoE2, ApoE3 and ApoE4. ApoE3 is considered to be the normal isoform, while ApoE2 and ApoE4 can each be dysfunctional. ApoE2 is defective in binding to LDL receptor (LDLR)[3]. Homozygosity for ApoE2 has been identified to be the primary cause of dysbetalipoproteinemia, which predisposes patients to the premature development of atherosclerosis[4]. ApoE4 is defective in recycling after internalized by cells[5]. Subjects homozygous for ApoE4 show elevated postprandial plasma lipids and higher susceptibility to coronary heart disease and Alzheimer disease[6].

ApoE-deficient mice develop atherosclerosis: The ApoE knockout (ApoE$^{-/-}$) mouse is one of the commonly used animal models for atherosclerosis studies. ApoE$^{-/-}$ mice develop hypercholesterolemia due to increased levels of plasma ApoB48-carrying lipoproteins (equivalent to human chylomicron remnants)[7-9], and develop atherosclerosis resembling human disease at histological features[10,11].

ApoE-deficient and ApoB48-containing lipoproteins induce foam cell formation: Previous findings from our laboratory demonstrated that incubation of mouse peritoneal macrophages (MPMs) with ApoE-deficient, ApoB48-containing (E$^-$/B48) lipoproteins resulted in intralysosomal lipoprotein accumulation, leading to foam cell formation[12]. We also demonstrated that the degradation rate of E$^-$/B48 lipoproteins in MPMs declined over time. Moreover, E$^-$/B48 lipoproteins reduced the protein levels of lysosomal acid lipase and cathepsin B[12]. Lysosomal acid lipase is the sole hydrolase responsible for cleavage of cholesteryl esters delivered to the lysosomes[13], while cathepsin B is one of the lysosomal proteases responsible for degradation of the endocytic proteins, including the protein components of lipoproteins[14]. Thus, reduction in lysosomal hydrolases might be a mechanism by which E$^-$/B48 lipoproteins trigger foam cell formation. We here demonstrate that induction of eIF-2α phosphorylation is a mechanism by which E$^-$/B48 lipoproteins inhibit lysosomal hydrolase expression.

Physiological significance of eIF-2α phosphorylation. Phosphorylation of eIF-2α is mediated by four different kinases[15]. One of them is known as PERK (RNA-dependent protein kinase-like ER kinase), which is activated by endoplasmic reticulum (ER) stress. The activated PERKs phosphorylate eIF-2α. The phosphorylated eIF-2α subsequently inhibits global protein synthesis. A sustained inhibition of global protein synthesis reduces the level of proteins with important functions, resulting in various disorders. For example, reduction in lysosomal hydrolase expression could repress the degradation of endocytic lipoproteins, leading to intralysosomal lipoprotein accumulation and foam cell formation. We demonstrated the causal role of eIF-2α phosphorylation in E$^-$/B48 lipoprotein-induced suppressive effect on lysosomal hydrolase expression.

Results and Discussion

1. Inhibition of eIF-2α phosphorylation by 2-AP delays the development of atherosclerosis in ApoE$^{-/-}$ mice: We find that oral feeding of 2-AP reduces the mean size of atherosclerotic lesions in the aorta root and the aorta tree by about 45% and 37%, respectively. Consistent with the smaller lesion size, the advanced lesions (e.g., fibrous caps and acellular areas) are reduced markedly in 2-AP-treated mice. Immunohistology studies show that the majority of cells are stained positively for phosphorylated eIF-2α in the lesional area of the untreated ApoE$^{-/-}$ control mice. In contrast, the phosphorylated eIF-2α immunostaining is significantly reduced in the atherosclerotic lesions of the 2-AP-treated mice. In this study, we also observed that the average plasma concentrations of total cholesterol, triglycerides, glucose and insulin were 486, 146, 125 mg/dl and 1.04 ng/ml, respectively, in 29-week-old ApoE$^{-/-}$ mice with 6-hr fasting, and that feeding 2-AP at a dose of 200 mg/kg BW once every other day for 24 weeks did not alter plasma lipid, glucose and insulin levels of ApoE$^{-/-}$ mice. Moreover, 2-AP treatment did not alter the body weight and food intake in ApoE$^{-/-}$ mice. These findings provide evidence that development of atherosclerosis in ApoE$^{-/-}$ mice is associated with an increased eIF-2α phosphorylation and that inhibition of eIF-2α phosphorylation via in vivo treatment with 2-AP delays the development of atherosclerosis.

2. Inhibition of eIF-2α phosphorylation by 2-AP represses E$^-$/B48 lipoprotein-induced foam cell formation in vitro. We previously reported that incubation of mouse peritonea macrophages (MPMs) with E$^-$/B48 lipoproteins induces lipid droplet accumulation in the cytoplasm. In some cells, E$^-$/B48 lipoproteins caused the cytoplasm to be almost entirely accumulated lipids, giving these cells a foam cell like appearance[12]. In the present study, we used a confocal microscopy to localize the accumulated lipids in MPMs and to assess the effect of 2-AP on this localization. Both untreated and lipoprotein-treated MPMs showed cytoplasmic lysosomal staining with LysoTracker stain (FIG. 2); however, the extent of staining was markedly greater in cells treated with E$^-$/B48 lipoproteins than in untreated cells. Untreated cells did not show DiI staining, whereas E$^-$/B48 lipoprotein-treated MPMs were significantly stained by DiI-labeled lipoprotein accumulation (FIG. 2). Furthermore, most of the DiI-stained lipid droplets co-localized with LysoTracker-labeling (FIG. 2), suggesting that the lipids accumulated in the cytoplasm were located in the lysosomes. Treatment of MPMs with 2-AP markedly reduced the level of staining with DiI, suggesting that inhibition of eIF-2α phosphorylation suppresses E$^-$/B48 lipoprotein-induced intralysosomal lipid accumulation and foam cell formation (FIG. 2).

3. ApoE-deficient lipoproteins induce eIF-2α phosphorylation. We observed that incubation of MPMs with E$^-$/B48 lipoproteins enhanced the phosphorylation of PERK and eIF-2α indicating that ApoE-deficient lipoprotein-induced foam cell formation coincides with an activation of PERK-eIF2α signaling cascade. We also observed that addition of 2-AP to culture medium or transfection of a nonphosphorylatable eIF2α mutant to MPMs attenuated E$^-$/B48 lipoprotein-induced eIF2α phosphorylation (not shown). ApoB-containing lipoproteins obtained from wild-type mice did not increase phosphorylation of PERK and eIF-2α.

4. Inhibition of eIF-2α phosphorylation increases macrophage lipoprotein degradation, and suppresses cholesterol ester and lipoprotein accumulation in macrophages. We observed that E$^-$/B48 lipoproteins induced a time-related accumulation of cholesterol ester and lipoproteins in MPMs, which is associated with a reduced degradation rate of E$^-$/B48 lipoproteins. The addition of 2-AP to culture medium or transfection of a nonphosphorylatable eIF-2α mutant to MPMs enhances E$^-$/B48 lipoprotein degradation, and reduces E$^-$/B48 lipoprotein and cholesterol ester accumulation (data not shown). These observations suggest a causal relationship between eIF-2α phosphorylation and lipoproteins and cholesterol accumulation.

5. Inhibition of eIF-2α phosphorylation attenuates E$^-$/B48 lipoprotein-induced suppressive effect on lysosomal hydrolases. We observed that incubation of MPMs with E$^-$/B48 lipoproteins inhibited global proteins synthesis, which was associated with a significantly reduced synthesis of lysosomal hydrolases, including cathepsin B and lysosomal acid lipase. We also observed that 2-AP and the nonphosphorylatable eIF-2α mutant attenuated the suppressive effect of E$^-$/B48 lipoproteins on lysosomal hydrolases (data not shown). It is highly likely that E$^-$/B48 lipoprotein-induced eIF-2α phosphorylation down-regulates macrophage lysosomal hydrolases, which in turn reduces the degradation of the lipid and protein components of E$^-$/B48 lipoproteins, leading to lipoprotein accumulation in the lysosomes and triggering foam cell formation.

6. Inhibition of eIF-2α phosphorylation attenuates E$^-$/B48 lipoprotein-induced suppression on mRNA translation. We observed that E$^-$/B48 lipoproteins reduced lysosomal hydrolases, due mainly to suppressing the translation of mRNAs encoding these proteins, and that 2-AP attenuated the suppressive effect of E$^-$/B48 lipoproteins on mRNA translation (data not shown).

7. Clinical relevance. Although a null mutation for ApoE has not been found in human subjects, dysfunctional polymorphisms of ApoE commonly exist in all racial and ethnic populations, with higher frequency in Africans. We observed that both ApoE3 and ApoE2 inhibit E$^-$/B48 lipoprotein-induced cholesterol ester accumulation, but that the inhibitory effect of ApoE3 is much more pronounced and sensitive than that for ApoE2. In addition, ApoE4 barely inhibits E$^-$/B48 lipoprotein-induced cholesterol accumulation. This finding is of considerable clinical relevance, because ApoE4- and ApoB48-containing lipoproteins (ApoE4-containing chylomicron remnants) commonly exist in human subjects. These data also hint that an absence of, or deficiency in, ApoE recycling might be a mechanism by which ApoE-deficient; ApoB48-containing lipoproteins induce macrophage cholesterol ester accumulation, via induction of eIF-2α phosphorylation.

SUMMARY: Without wishing to be bound by any underlying theory of the invention, the schematic diagram of FIG. 3 proposes the mechanism how 2-AP represses atherosclerosis. Interaction of macrophages with E$^-$/B48 lipoproteins induces eIF-2α phosphorylation, which in turn inhibits overall mRNA translation, reducing lysosomal hydrolase synthesis. A sustained reduction in lysosomal hydrolases results in a decreased degradation of lipoproteins, leading to lipoprotein accumulation in the macrophages and inducing foam cell formation and atherosclerosis development. The interventions, including 2-AP and nonphosphorylatable eIF-2α mutant, inhibit eIF-2α phosphorylation, inhibit foam cell formation and atherosclerosis development, and therefore will be used to treat atherosclerosis-related cardiovascular diseases.

REFERENCES

1. Stary H C, Chandler A B, Dinsmore R E, Fuster V, Glagov S, Insull W Jr, Rosenfeld M E, Schwartz C J, Wagner W D, Wissler R W. A definition of advanced types of atherosclerotic lesions and a histological classification of atherosclerosis. A report from the Committee on Vascular Lesions of the Council on Arteriosclerosis, American Heart Association [review]. *Circulation*. 1995; 92:1355-1374.
2. McGill H C. Overview. In: Fuster V, Ross R, Topol E J, eds. *Atherosclerosis and coronary artery disease*. Philadelphia: Lippincott-Raven Publishers; 1999. p. 25-41.
3. Mahley R W, Rall S C, Jr. Apolipoprotein E: far more than a lipid transport protein. *Annu Rev Genomics Hum Genet*. 2000; 1:507-537.
4. Mahley R W, Huang Y, Rall S C, Jr. Pathogenesis of type III hyperlipoproteinemia (dysbetalipoproteinemia). Questions, quandaries, and paradoxes. *J Lipid Res*. 1999; 40:1933-1949.

5. Heeren J, Grewal T, Jackle S, Beisiegel U. Recycling of apolipoprotein E and lipoprotein lipase through endosomal compartments in vivo. *J Biol Chem.* 2001; 276:42333-42338.
6. Heeren J, Beisiegel U, Grewal T. Apolipoprotein E recycling: implications for dyslipidemia and atherosclerosis. *Arterioscler Thromb Vasc Biol.* 2006; 26:442-448.
7. Piedrahita J A, Zhang S H, Hagaman J R, Oliver P M, Maeda N. Generation of mice carrying a mutant apolipoprotein E gene inactivated by gene targeting in embryonic stem cells. *Proc Natl Acad Sci USA.* 1992; 89:4471-4475.
8. Guo Z M, Mitchell-Raymundo F, Yang H, Ikeno Y, Nelson J, Diaz V, Richardson A, Reddick R. Dietary restriction reduces atherosclerosis and oxidative stress in the aorta of apolipoprotein E-deficient mice. *Mech Ageing Dev.* 2002; 123:1121-1131.
9. Farese R V, Jr., Veniant M M, Cham C M, Flynn L M, Pierotti V, Loring J F, Traber M, Ruland S, Stokowski R S, Huszar D, Young S G. Phenotypic analysis of mice expressing exclusively apolipoprotein B48 or apolipoprotein B100. *Proc Natl Acad Sci USA.* 1996; 93:6393-6398.
10. Reddick R L, Zhang S, Maeda N. Atherosclerosis in Mice Lacking Apo E: Evaluation of Lesional Development and Progression. *Arterioscler Thromb.* 1994; 14:141-147.
11. Carmeliet P, Moons L, Collen D. Mouse models of angiogenesis, arterial stenosis, atherosclerosis and hemostasis. *Cardiovasc Res.* 1998; 39:8-33.
12. Wu D F, Sharan C, Yang H, Goodwin J S, Grabowski G A, Guo Z M. Apolipoprotein E-deficient lipoproteins induce foam cell formation by downregulation of lysosomal hydrolases in macrophages. *J Lipid Res.* 2007.
13. Zschenker O, Illies T, Ameis D. Overexpression of lysosomal acid lipase and other proteins in atherosclerosis. *J Biochem* (Tokyo). 2006; 140:23-38.
14. O'Neil J, Hoppe G, Hoff H F. Phospholipids in oxidized low density lipoproteins perturb the ability of macrophages to degrade internalized macromolecules and reduce intracellular cathepsin B activity. *Atherosclerosis.* 2003; 169: 215-224.
15. Wek R C, Jiang H Y, Anthony T G. Coping with stress: eIF2 kinases and translational control. *Biochem Soc Trans.* 2006; 34:7-11.

The foregoing is illustrative of the present invention, and is not to be construed as limiting thereof. The invention is defined by the following claims, with equivalents of the claims to be included therein.

What is claimed is:

1. A method of treating atherosclerosis or hyperlipidemia in a human subject in need thereof, comprising orally administering to said subject 2-aminopurine or a pharmaceutically acceptable salt thereof in an effective amount, wherein said human subject has an ApoE2 or ApoE4 isoform.

2. The method of claim 1, wherein said administering step is carried out by orally administering to said subject a pharmaceutical formulation comprising 2-aminopurine or a pharmaceutically acceptable salt thereof in a pharmaceutically acceptable carrier.

3. The method of claim 2, wherein said formulation is in the form of a capsule, cachet, lozenge, or tablet.

4. The method of claim 2, wherein said formulation is in the form of a solution or suspension.

5. The method of claim 1, further comprising concurrently administering to said subject at least one additional antiatherosclerosis active agent.

6. The method of claim 5, wherein said additional active agent is selected from the group consisting of statins, bile acid sequestrants, fibrates, niacin, ezetimibe, phytosterols, CETP Inhibitors, squalene synthase inhibitors, ApoA-1 Milano, and AGI-1067.

7. The method of claim 1, wherein said human subject is homozygous for the ApoE2 isoform.

8. The method of claim 1, wherein said human subject is homozygous for the ApoE4 isoform.

* * * * *